United States Patent
Leroux et al.

(10) Patent No.: US 9,518,894 B2
(45) Date of Patent: Dec. 13, 2016

(54) DEVICE FOR MEASURING VIBRATION AMPLITUDES OF THE BLADE TIPS IN A TURBOMACHINE

(71) Applicant: SNECMA, Paris (FR)

(72) Inventors: Andre Leroux, Samois sur Seine (FR); Serge Del Arco, Hericy (FR); Olivier Follerot, Paris (FR); Michel Herbault, Le Mee Sur Seine (FR); Philippe Armand Hugbart, Suvry Courtry (FR); Fabien Pouchard, Brunoy (FR); Etienne Tulie, Soisy sur Seine (FR)

(73) Assignee: SNECMA, Paris (FR)

( * ) Notice: Subject to any disclaimer, the term of this patent is extended or adjusted under 35 U.S.C. 154(b) by 950 days.

(21) Appl. No.: 13/888,715

(22) Filed: May 7, 2013

(65) Prior Publication Data
US 2014/0356132 A1    Dec. 4, 2014

(30) Foreign Application Priority Data

May 15, 2012  (FR) ...................................... 12 54448

(51) Int. Cl.
*G01M 15/14*  (2006.01)
*G01H 1/00*  (2006.01)
(Continued)

(52) U.S. Cl.
CPC ............ *G01M 15/14* (2013.01); *F01D 21/003* (2013.01); *G01B 11/14* (2013.01); *G01H 1/006* (2013.01);
(Continued)

(58) Field of Classification Search
CPC ........ F01D 21/003; G01M 15/14; G01M 7/00; G01B 11/14; G01H 9/006; G01H 1/006; G01N 21/1702; G01N 2021/1706; G01N 2201/08

See application file for complete search history.

(56) References Cited

U.S. PATENT DOCUMENTS 5,201,227 A    4/1993   Iinuma et al.
5,349,850 A *  9/1994   Young ................... G01B 11/00
                                                      73/112.01
(Continued)

FOREIGN PATENT DOCUMENTS

DE         196 01 225 C1    6/1997
DE    10 2009 017 796 A1   10/2010
(Continued)

OTHER PUBLICATIONS

French Preliminary Search Report issued Feb. 8, 2013 in French Application 12 54448, filed May 15, 2012 ( with English Translation of Category of Cited Documents).

(Continued)

*Primary Examiner* — Dwayne J White
*Assistant Examiner* — Adam W Brown
(74) *Attorney, Agent, or Firm* — Oblon, McClelland, Maier & Neustadt, L.L.P.

(57) ABSTRACT

A device for measuring vibration amplitudes of the blade tips in a turbomachine is provided. The device includes a support mounted in an orifice of a casing of a turbomachine, in which are housed two optical guides for the emission and reception of a light signal exiting inside the casing across from the tips of the blades of a turbine wheel Each optical guide includes an optical fiber connected by a mechanical connector to a needle of which the core is made of a material able to transmit a light signal and which is resistant to temperatures less than or equal to 1100° C. and which exits at its distal end in the casing across from the blade tips.

15 Claims, 4 Drawing Sheets

(51) Int. Cl.
*G01H 9/00* (2006.01)
*G01M 7/00* (2006.01)
*G01B 11/14* (2006.01)
*F01D 21/00* (2006.01)
*G01N 21/17* (2006.01)

(52) U.S. Cl.
CPC ............... *G01H 9/006* (2013.01); *G01M 7/00* (2013.01); *G01N 21/1702* (2013.01); *G01N 2021/1706* (2013.01); *G01N 2201/08* (2013.01)

(56) References Cited

U.S. PATENT DOCUMENTS

| | | | |
|---|---|---|---|
| 5,557,099 A | | 9/1996 | Zielinski et al. |
| 7,707,889 B2 * | | 5/2010 | Maurus .................. G01H 9/00 |
| | | | 250/458.1 |
| 8,164,761 B2 * | | 4/2012 | Kominsky .............. F01D 11/20 |
| | | | 250/559.22 |
| 2009/0078053 A1 | | 3/2009 | Twerdochlib |
| 2011/0069165 A1 * | | 3/2011 | Zombo ................. F01D 21/003 |
| | | | 348/82 |

FOREIGN PATENT DOCUMENTS

| | | |
|---|---|---|
| EP | 2 299 235 A1 | 3/2011 |
| FR | 2 714 488 A1 | 6/1995 |
| GB | 2 342 988 | 4/2000 |

OTHER PUBLICATIONS

M Zielinski et al. "Noncontact vibration measurements on compressor rotor blades", Measurement Science and Technology vol. 11. No. 7, 2000, pp. 847-856.

Evangelos V. Diatzikis et al. "In-situ dynamic measuring system to measure the vibratory and translational displacement of the airfoil modes of a combustion turbine compressor vane via an optical non-contact method", Proc of SPIE vol. 7677, 2010, pp. 1-13.

* cited by examiner

DEVICE FOR MEASURING VIBRATION AMPLITUDES OF THE BLADE TIPS IN A TURBOMACHINE

BACKGROUND OF THE INVENTION

1. Field of the Invention

This invention relates to a device for measuring vibration amplitudes of the blade tips in a turbomachine such as an aircraft turbojet or a turboprop engine for aircraft.

2. Description of the Related Art

In a known manner, a turbomachine comprises a turbine of which the rotor is driven in rotation by the flow of hot gases exiting from an annular combustion chamber arranged upstream. The rotor carries one or several wheels of blades arranged alternately with annular rows of fixed blades in a casing.

During the operation of the turbomachine, it is important to know the deformation of the mobile blades. For this purpose, it is known to mount on the casing sensors of which the sensitive element is arranged to the right of the mobile blades. The sensitive element of each sensor makes it possible to detect the passage of a blade tip (known as "tip timing") in order to determine through comparison between the theoretical time of passage of a blade tip and the measured time of passing the deformation mode of the blade, in bending, in twisting, etc., as well as the intensity of the deformation.

The applicant has already proposed in application FR1155983 to use sensors of the capacitive type in a blower or a low-pressure compressor of a turbomachine.

However, these sensors cannot be mounted in a turbine due to the high temperature present therein and which is of a magnitude of 1000° C. In addition, in the current state of the art, these capacitive sensors have a low temporal resolution which does not make it possible to obtain deformation measurements less than 100 µm, which corresponds to a magnitude of deformations that the tips of the blades can potentially be subjected to when the latter are made of composite material having a ceramic matrix.

In order to overcome these difficulties, it has been proposed to use optical probes to detect the times of passage of the blades. Conventionally, these probes include at least two optical fibres of which one is connected to means for emitting a source of light and of which the other receives and transmits the light reflected by the blade tip to means for processing. However, these optical probes initially designed for an integration into a turbomachine compressor are poorly adapted for use in the hot environment of the turbine. It would be possible to cool them during operation by supplying for example cold air from the high-pressure compressor arranged upstream of the combustion chamber. However, such a solution would highly penalise the output and the thrust produced by the turbomachine by taking the compressed air which is used for the combustion.

BRIEF SUMMARY OF THE INVENTION

The purpose of the invention in particular is to provide a simple, economical and effective solution to these different problems.

For this purpose, it proposes a device for measuring vibration amplitudes of the blade tips in a turbomachine, comprising a support mounted in an orifice of a casing of a turbomachine and wherein are housed two optical guides exiting inside the casing across from the tips of the blades of a turbine wheel, with one of the optical guides being connected to a source of light for the propagation of a light signal to the blade tips and the other optical guide being connected to means for processing and analysing the light signal reflected by the blade tips, characterised in that each optical guide comprises an optical fibre connected by a mechanical connector to a rigid needle of which the core is made of a material able to transmit a light signal and which exits at its distal end inside the casing across from the blade tips.

In the device according to the invention, a rigid needle having a core made of a material able to transmit a light signal and resistant to temperatures equal to 1100° C. can easily be integrated into the hot and turbulent environment of the turbine in operation, and easily adjustable at a short distance from the ends of the blades. Each needle is connected to an optical fibre of which the flexibility allows it to be arranged in a complex environment such as that of a turbomachine.

The device according to the invention moreover comprises two needles and two optical fibres that are separate and not a single needle connected at its proximal end to two optical fibres as the interface between the needle and the optical fibre induces a strong reflection of the light signal which is stronger than the signal reflected by a blade tip, which would cause difficulties in detecting the signal reflected by the blade tips.

Preferentially, the support is mounted in an orifice of a boss of the casing and comprises a flange formed on its external surface whereon is mounted with radial abutment from the exterior a member for blocking the support on the boss, with this member being fixed in a detachable manner to the boss.

In a particular embodiment of the invention, the member for blocking is formed by a nut mounted around the support and screwed onto a threaded internal surface of the orifice of the boss.

According to another characteristic of the invention, each connector comprises an axially split tube wherein are maintained in contact the proximal end of the needle and the distal end of the optical fibre.

This tube provides an end-to-end maintaining by tightening the proximal end of the needle and the distal end of the optical fibre for the transmission of the light signal.

According to another characteristic of the invention, the support comprises two tubular housings converging towards the interior of the turbomachine on the blade tips and exiting inside the casing and wherein are inserted from the exterior the needles of the optical guides.

With this arrangement, it is possible to arrange the two needles so that their axes converge towards the blade tips, which makes it possible to guarantee that a light signal reflected by a blade tip and not by another portion of the blade will be detected.

According to another characteristic of the invention, each optical guide comprises a bushing mounted around the proximal end portion of the needle, with this bushing comprising an external annular edge coming to abut radially towards the interior on an internal radial shoulder of the housing of the support wherein is mounted the needle of the optical guide.

According to another characteristic of the invention, each needle is retained radially towards the exterior in its housing by a cylindrical part mounted around the distal end portion of the optical fibre and in axial abutment in the direction of the needle on an external annular edge of said distal end portion, with the cylindrical part comprising a threaded external surface which is screwed into a threaded internal surface of the housing.

The needle of each optical guide is as such maintained radially in its housing, by the external annular edge of the bushing coming to abut on the internal radial shoulder of the housing and by the cylindrical part screwed into the housing and applied on the annular edge of the distal end portion of the optical fibre to which the needle is connected.

The annular edge of the distal end portion of each optical fibre can be formed with an added part crimped around said distal end portion.

In a particular embodiment of the invention, the core of the needle is surrounded by a metal sheath, such as titanium.

Advantageously, the distal surface of the core of the needle is offset radially towards the interior in relation to the distal end of the sheath, which prevents the formation of metal oxide on the distal surface of the core of the needle.

In a particular embodiment of the invention, the core of the needle is made of a material that can resist a temperature equal to 1100° C.

The core is preferentially made of sapphire. The use of sapphire allows for the insertion of the needles of the device inside a turbine without the risk of thermal degradation due to the fact that sapphire resists high temperatures well.

The utilisation of a metal sheath having a low coefficient of thermal expansion makes it possible to limit the expansion of the needle in its housing. In addition, sapphire has a very low coefficient of thermal expansion, which makes it possible to limit the differences in thermal expansion between the metal sheath and the core made of sapphire.

According to the invention, the source of light emits a beam with a wavelength centred on a wavelength that is less than the wavelengths of the radiations emitted in the turbine. Advantageously, the means for processing and analysing include a low-pass filter for the filtering of wavelengths greater than the wavelength of the source of light. In a particular embodiment, the source of light emits a beam of wavelength centred on 405 nm.

The invention further relates to a turbomachine comprising a device for measuring such as described hereinabove.

The invention further proposes a system for measuring the vibration amplitudes of the blade tips in a turbomachine, characterised in that it comprises a device such as described hereinabove, with one of the optical guides being connected by its proximal end to a laser source and the other of the optical guides being connected at distal end to means for amplifying, sampling, converting and transferring data to means for processing.

BRIEF DESCRIPTION OF THE SEVERAL VIEWS OF THE DRAWINGS

Other advantages and characteristics of the invention shall appear when reading the following description given by way of a non-restricted example and in reference to the annexed drawings wherein.

DETAILED DESCRIPTION OF THE INVENTION

Figure 1:
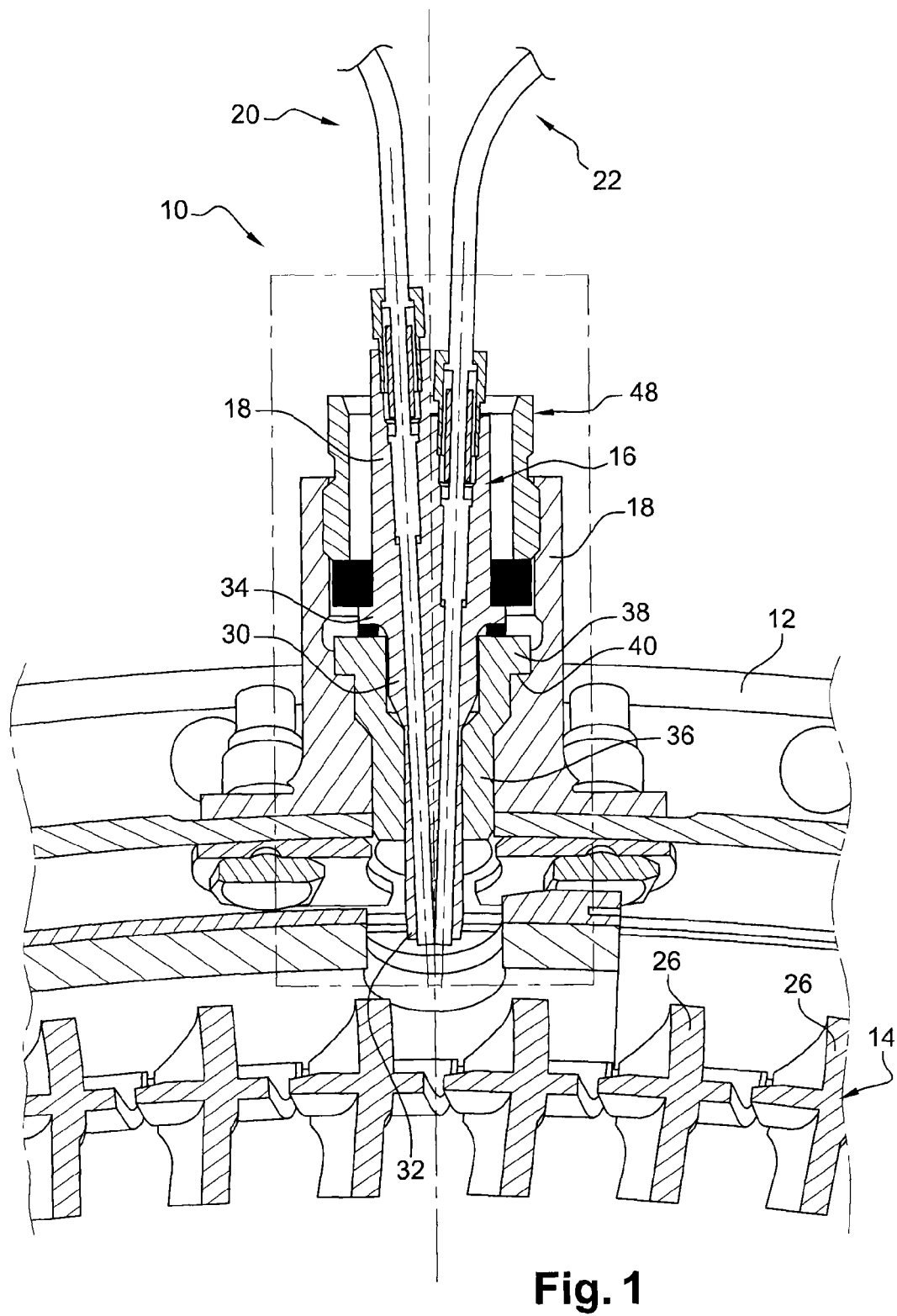
FIG. 1 is a cross-section partial diagrammatical half-view of the device according to the invention arranged on a turbine casing of a turbomachine.

Reference is first made to FIG. 1 which shows a device 10 according to the invention mounted on a casing surrounding exteriorly annular rows of fixed blades and wheels of blades arranged axially alternately with one another. FIG. 1 is a view according to a cut plane perpendicular to the axis of the turbine, passing through an impeller 14 and through the device according to the invention.

The device 10 according to the invention comprises a support 16 mounted in a radial orifice of a boss 18 of the casing 12. Two optical guides 20, 22 are mounted in the support 16 and exiting at their distal ends inside the casing 12, with one 20 of the optical guides being an optical guide for emitting 20 connected to a source of light for the propagation of a light signal to the blade tips 26 and the other being an optical guide for receiving 22 which receives the signal reflected by the blade tips 26 and transfers it to a processing unit. The measurement chain associated to the device 10 shall be described in more detail later.

The support 16 comprises three substantially cylindrical portions, a first proximal portion 28 of outer diameter greater than that of the second intermediary portion 30 itself with an outer diameter greater than that of the third distal portion 32. The first proximal portion 28 and the second intermediary portion 30 of the support 16 are separated from one another by an annular flange 34 formed as a protrusion radially towards the exterior on the outside edge of the support 16.

The second intermediary portion 30 and third distal portion 32 of the support 16 are mounted in an opening of a centring part 36 engaged from the exterior in the boss and blocked radially towards the interior by an external annular edge 38 coming to abut on an internal shoulder 40 of the boss 18. The centring part 36 comprises a first portion 42 of which the inner diameter allows for the mounting of the second intermediary portion 30 of the support 16 and a second portion 44 of which the inner diameter is smaller and allows the passage only of the third distal portion 32 of the support 16, in such a way as to block radially towards the interior the support 16 in the boss 18.

An annular wedge 46 is inserted between the centring part 36 and the flange 34 of the support 16. The modification of the radial thickness of the wedge makes it possible to adjust the radial position of the distal ends of the optical guides 20, 22 inside the casing 12, in relation to the blade tips.

A nut 48 is mounted around the first proximal portion 28 of the support 16 and is screwed onto a threaded internal surface of the radially external end of the orifice of the boss 18. This nut 48 comes to abut against the flange 34 of the support and provides a blocking radially towards the exterior of the support 16 in the boss 18.

Figure 2:
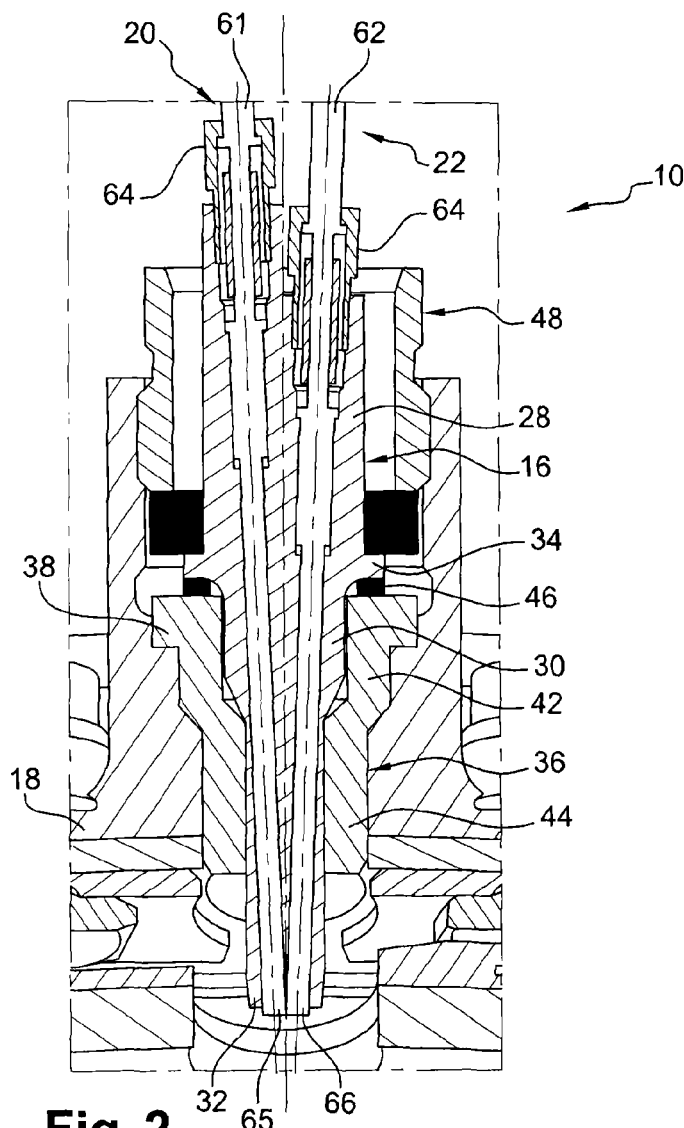
FIG. 2 is a diagrammatical view on a larger scale of the zone delimited with dotted line in FIG. 1.
Figure 3:
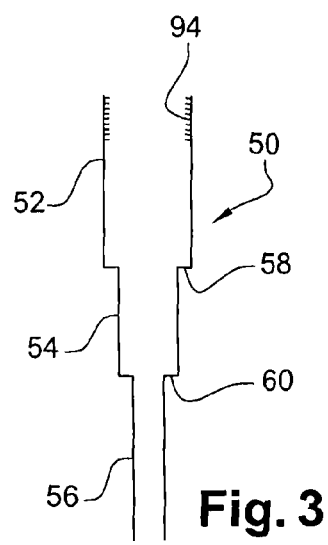
FIG. 3 is a diagrammatical view of a housing of the support of the device according to the invention.

The support 16 comprises two separate tubular housings 50 (an isolated diagrammatical representation of a housing is shown in FIG. 3) exiting inside the casing and of which the axes converge towards the interior of the turbomachine and are cut on a blade tip when a blade is aligned with the axis of the support 16. Each housing is formed of three tubular portions 52, 54, 56 of which the internal sections decrease radially towards the interior and are separated from one another by radial shoulders 58, 60 of the internal surface of the housings 50 (FIGS. 2 and 3).

The first 52 and second 54 tubular portions of each housing 50 extend in the first portion 28 of the support 16 and the third tubular portion 56 of each housing 50 extending partially in the first portion 28 of the support 16 and in the second and third portions 30, 32 of the support.

Figure 6:
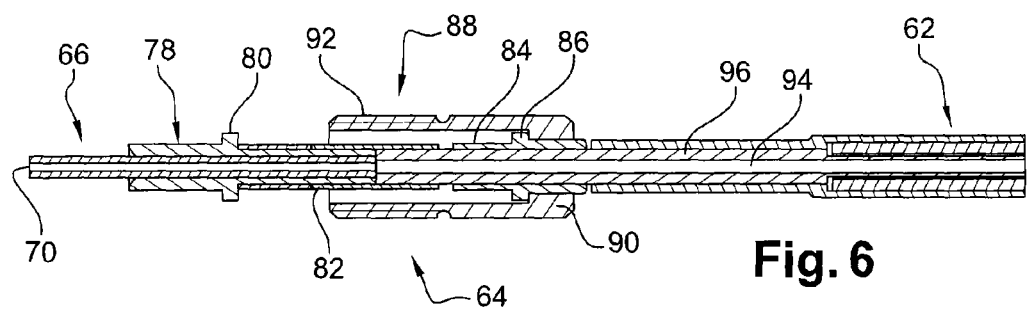
FIG. 6 is a cross-section diagrammatical view of an optical guide of the device according to the invention.
Figure 7:
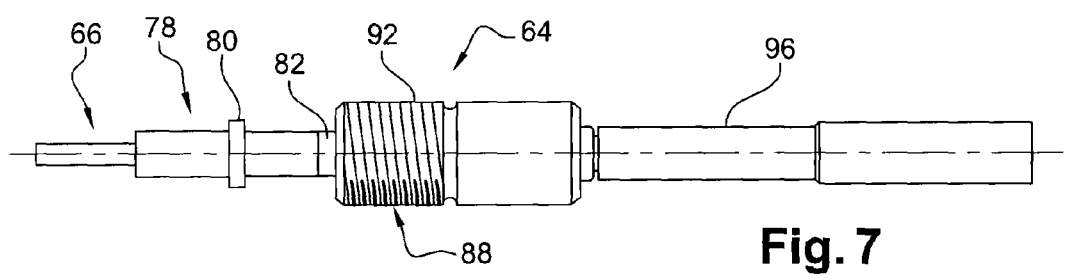
FIGS. 7 and 8 are diagrammatical side views of the optical guide of FIG. 4.
Figure 8:
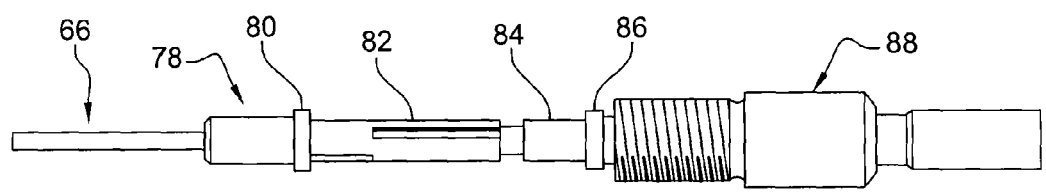
Figure 9:
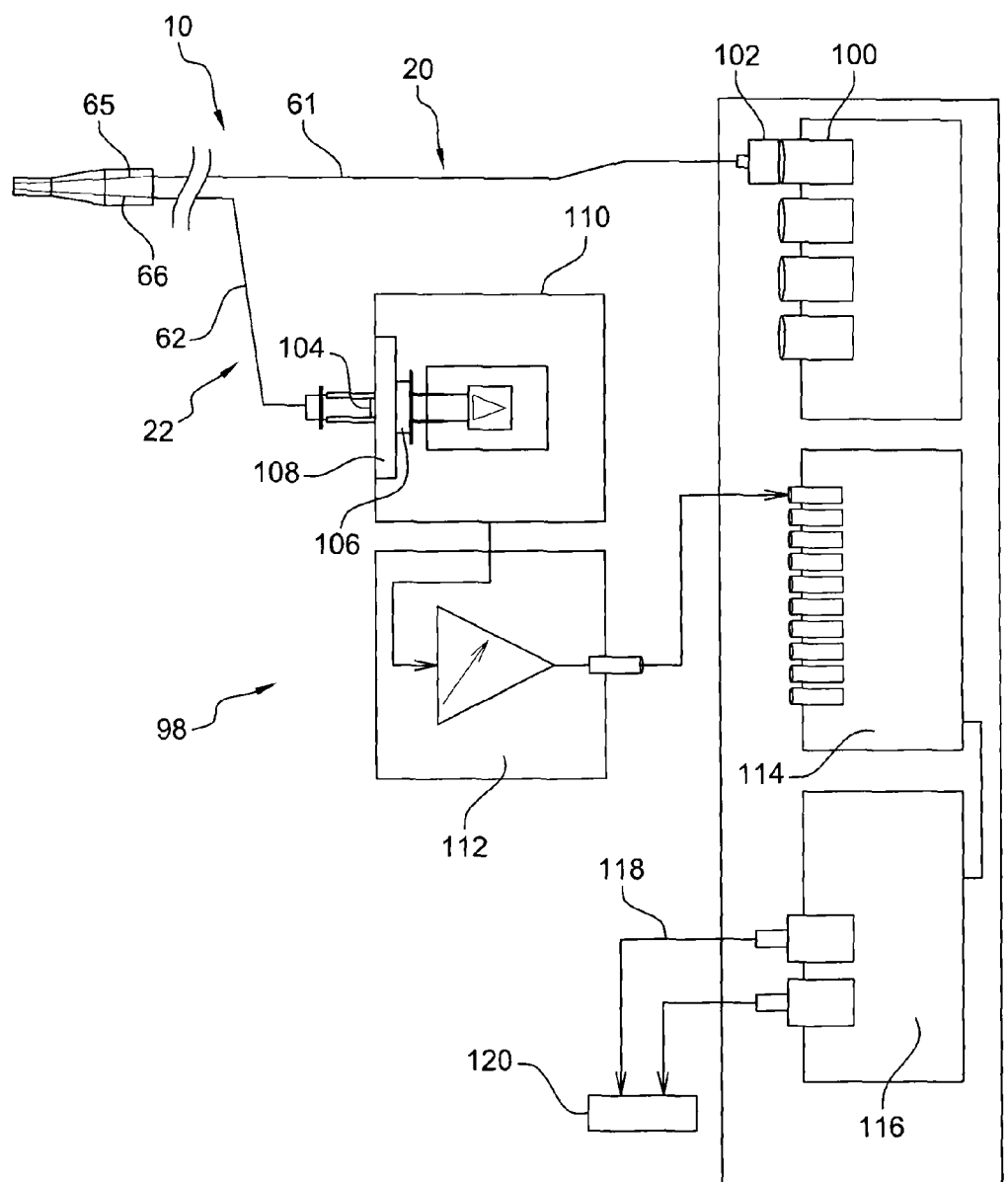
FIG. 9 is a diagrammatical representation of a measurement chain comprising the device according to the invention.

Each optical guide 20, 22 is formed by an optical fibre 61, 62 connected by a connector 64 to a needle 65, 66 inserted into a housing 50 of the support 16 and exiting radially towards the interior in the casing 12 across from the tips 26 of blades (FIGS. 1 and 6 to 7).

Figure 4:
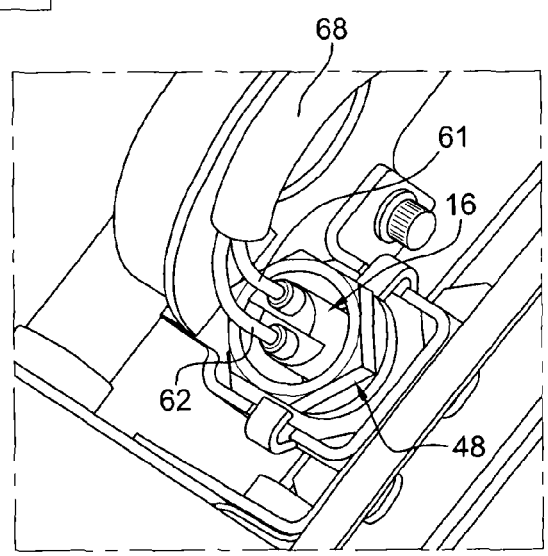
FIG. 4 is a diagrammatical view in perspective from the exterior of the casing of the device of FIG. 1.

The optical fibres 61, 62 of the optical guides 20, 22 are housed in a flexible protective sheath 68 (FIG.4).

The description given hereinbelow in reference to the optical guide for receiving 22 applies identically to the optical guide for emitting 20.

Figure 5:
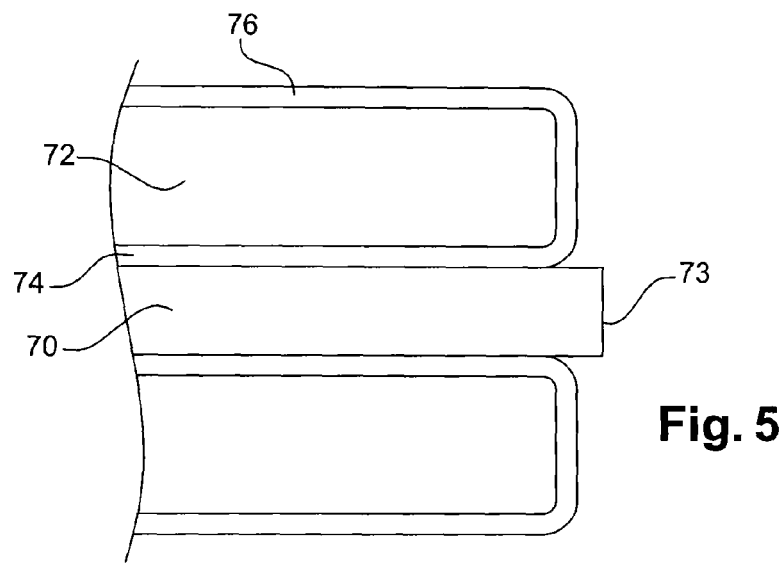
FIG. 5 is a diagrammatical view of the distal end of an optical guide of the device according to the invention.

The needle 66 comprises a core 70 made of sapphire surrounded by a metal sheath 72 having a low coefficient of thermal expansion which is less than the coefficient of thermal expansion of the sapphire in such a way as to limit the expansion of the sapphire core in the support 16. The sapphire core 70 is made integral with the metal sheath 72 by means of a ceramic glue 74 that resists high temperatures (FIGS. 5 and 6).

In operation, the surface of the metal layer directly in contact with the hot gases is covered with a layer of metal oxide 76, such as for example a layer of titanium oxide when the sheath is made of titanium (FIG. 4). The distal surface 73 of the sapphire core exiting inside the casing is offset radially towards the interior in relation to the metal sheath, for example by approximately 0.5 mm, in such a way as to prevent the layer of oxide from partially covering the distal surface of the sapphire core.

A bushing 78 is mounted around the proximal end portion of the needle 66. This bushing 78 comprises an annular edge 80 intended to abut radially towards the interior on the radial shoulder 58 separating the first and second 54 tubular portions of the housing 50 (FIGS. 3 and 5). The proximal end portion of the needle extends beyond the bushing 78 on the side of the annular edge 80.

An annular part 84 is crimped around the proximal end portion of the optical fibre 62 and includes an external annular edge 86.

A tube 82 split according to its axis is mounted tight for a portion around the distal end of the optical fibre 62 and for the other opposite portion around the proximal end of the needle 66. This split tube 82 provides an end-to-end maintaining of the proximal end of the needle 66 and of the distal end of the optical fibre for the optical transmission and a maintaining in alignment of the bushing 78 and of the annular part 84 for the mounting in the tubular housing 50.

A cylindrical part 88 is mounted around the proximal end portion of the optical fibre 62. This cylindrical part 88 comprises an annular edge 90 at its proximal end coming to abut on the annular edge 86 of the annular part crimped on the proximal end portion of the optical fibre 62. The distal portion of the cylindrical part 88 comprises a threading 92 on its external surface for its screwing into a corresponding threading 94 of the internal surface of the housing (FIGS. 2, 3, 5 and 6).

As such, when the needle 66 is inserted into its housing 50, it is blocked radially towards the interior by the annular edge 80 of the bushing 78 pressing against the shoulder 58 of the housing 50 and radially towards the exterior by the annular edge 86 of the crimped part 84 pressing on the annular edge 90 of the cylindrical part 88 screwed into the housing 50.

As shown in FIG. 1, the shoulders 58 of the support 16 are positioned along each housing and the lengths of the needles 66 are determined in such a way that the distal ends of the needles 66 are flush with the radially internal end of the third distal portion 32 of the support 16. In this way, the needles 66 are protected by the support 16 and their heating during operation is limited.

The two needles 65, 66 can have different lengths (FIG. 2) or be identical according to the space available around the turbomachine.

The optical fibre 62 comprises a central portion 94 made from a material providing the propagation of the light signal such as silica and is surrounded by a sheath 96 that resists high temperatures made from a metal material such as copper, aluminium or gold.

FIG. 7 shows a system 98 for measuring vibration amplitudes of the blade tips wherein is integrated the device 10 described hereinabove.

The optical fibre 61 of the optical guide for emitting 20 is connected to its end opposite the needle to a laser source 100 by the intermediary of a connector 102 comprising an optical lens and a centring sleeve. The light signal transmitted by the optical fibre 61 and the needle 65 of the optical guide for emitting 20 is reflected by a blade tip and transmitted to the needle 66 of the optical guide for receiving 22 then is propagated in the optical fibre 62 for reception. The light signal then passes through a lens 104 providing a focusing of the light signal on a photodiode 106 allowing for a conversion of the light signal into an electrical signal. A low-pass filter 108 is inserted between the focusing lens 104 and the photodiode 106 and is configured to eliminate the wavelengths greater than the wavelength of the laser radiation. The electrical signal is then transmitted to a preamplifier 110 and to an adjustable gain amplifier 112, to a sampling board 114 then to a board 116 for converting the electrical signal into an optical signal for its transfer by optical cable 118 to the means for processing 120 such as for example full authority digital engine control, also known by its acronym FADEC.

According to the invention, the use of a sapphire core for each needle 65, 66 allows for a mounting of the needles 65 66 inside the turbine without the risk of thermal degradation of the needle 65, 66 since sapphire is a material that resists the high temperatures that are present in a turbine and which are of a magnitude of 1000° C.

In addition, the use of a needle connected to a flexible optical fibre makes it possible to guarantee an assembly of the device according to the invention in the complex three-dimensional environment of the casing of the turbine.

In a practical example, the source of light can emit a laser beam with a power of about 120 mW and with a wavelength centred on 405 nm. This wavelength is selected to be less than the wavelengths of the radiation emitted by the flow of hot gases exiting the combustion chamber. The low-pass filter is configured to eliminate all of the wavelengths greater than 450 nm. In this way, the wavelengths located in the red and infrared ranges, emitted by the hot gases coming from the combustion chamber and the hot environment of the turbine, are eliminated.

In a practical embodiment of the invention, the metal sheath surrounding the sapphire core is made of titanium which is covered during operation with a layer of titanium oxide. The bonding glue of the sapphire core with the metal sheath is for example Ceramabond 569®.

The invention claimed is:

1. A device for measuring vibration amplitudes of the blade tips in a turbomachine, comprising:
   a support mounted in an orifice of a casing of a turbomachine and wherein are housed first and second optical guides exiting the casing across from the tips of the blades of a turbine wheel, with the first optical guide being connected to a source of light for the propagation of a light signal to the blade tips and the second optical guide being connected to means for processing and analysing the light signal reflected by the blade tips,
   wherein each optical guide comprises an optical fiber connected at one end by a mechanical connector to a rigid needle of which a core is made of a material able to transmit a light signal and which is resistant to temperatures equal to 1100° C. and which exits at a distal end thereof inside the casing across from the blade tips.

2. The device according to claim 1, wherein the support is mounted in an orifice of a boss of the casing and comprises a flange formed on an external surface thereof, on which external surface is mounted radially abutting from an exterior a member for blocking the support on the boss, with the member for blocking being fixed in a detachable manner to the boss.

3. The device according to claim 2, wherein the member for blocking is formed by a nut mounted around the support and screwed onto a threaded internal surface of the orifice of the boss.

4. The device according to claim 1, wherein each connector comprises an axially split tube wherein are maintained in contact the proximal end of the needle and the distal end of the optical fiber.

5. The device according to claim 1, wherein the support comprises two tubular housings converging towards an interior of the turbomachine on the blade tips and exiting inside the casing and wherein are inserted from an exterior the needles of the optical guides.

6. The device according to claim 5, wherein each optical guide comprises a bushing mounted around a proximal end portion of the needle, with the bushing comprising an external annular edge coming to abut radially towards an interior on an internal radial shoulder of the housing of the support wherein is mounted the needle of the optical guide.

7. The device according to claim 5, wherein each needle is retained radially towards an exterior in the housing by a cylindrical part mounted around the distal end portion of the optical fiber and in axial abutment in a direction of the needle on an external annular edge of said distal end portion, the cylindrical part comprising a threading on an external surface thereof for screwing into a corresponding threading of an internal surface of the housing.

8. The device according to claim 7, wherein the annular edge of the distal end portion of each optical fiber is formed with an added part crimped around said distal end portion.

9. The device according to claim 1, wherein the core of the needle is surrounded by a metal sheath.

10. The device according to claim 9, wherein a distal surface of the core of the needle is offset radially towards an interior in relation to a distal end of the sheath.

11. The device according to claim 9, wherein the core of the needle is surrounded by a titanium sheath.

12. The device according to claim 1, wherein the core is made of sapphire.

13. A turbomachine comprising the device according to claim 1.

14. A system for measuring vibration amplitudes of the blade tips in a turbomachine, comprising the device according to claim 1, with the first optical guide being connected at a proximal end thereof to a laser source and the second optical guide being connected at the distal end thereof to means for amplifying, sampling, converting and transferring data to the means for processing.

15. A device for measuring vibration amplitudes of the blade tips in a turbomachine, comprising:
   a support mounted in an orifice of a casing of a turbomachine and wherein are housed first and second optical guides exiting inside the casing across from the tips of the blades of a turbine wheel, with the first optical guide being connected to a source of light for the propagation of a light signal to the blade tips and the second optical guide being connected to means for processing and analysing the light signal reflected by the blade tips,
   wherein each optical guide comprises an optical fiber connected by a mechanical connector to a rigid needle of which a core is made of a material able to transmit a light signal and which is resistant to temperatures equal to 1100° C. and which exits at a distal end thereof inside the casing across from the blade tips, and
   wherein each connector comprises an axially split tube wherein are maintained in contact the proximal end of the needle and the distal end of the optical fiber.

* * * * *